US012758353B2

(12) United States Patent
Ng et al.

(10) Patent No.: US 12,758,353 B2
(45) Date of Patent: Oct. 13, 2026

(54) FIDUCIAL MARKER SET, A METHOD OF DETERMINING A POSITION OF THE SAME AND A CONTROL SYSTEM

(71) Applicant: NDR Medical Technology Private Limited, Singapore (SG)

(72) Inventors: Ka Wei Ng, Singapore (SG); Siang Huei Leong, Singapore (SG); Jin Quan Goh, Singapore (SG)

(73) Assignee: NDR Medical Technology Private Limited, Singapore (SG)

( * ) Notice: Subject to any disclaimer, the term of this patent is extended or adjusted under 35 U.S.C. 154(b) by 87 days.

(21) Appl. No.: 18/574,669

(22) PCT Filed: Jun. 28, 2021

(86) PCT No.: PCT/SG2021/050376
§ 371 (c)(1),
(2) Date: Dec. 27, 2023

(87) PCT Pub. No.: WO2023/277783
PCT Pub. Date: Jan. 5, 2023

(65) Prior Publication Data

US 2024/0315798 A1 Sep. 26, 2024

(51) Int. Cl.
*A61B 90/00* (2016.01)
*A61B 34/20* (2016.01)
*A61B 34/32* (2016.01)

(52) U.S. Cl.
CPC .............. *A61B 90/39* (2016.02); *A61B 34/32* (2016.02); *A61B 2034/2065* (2016.02); *A61B 2090/3966* (2016.02)

(58) Field of Classification Search
CPC .......... G06T 2207/30204; A61B 34/30; A61B 34/32
See application file for complete search history.

(56) References Cited

U.S. PATENT DOCUMENTS 4,945,914 A * 8/1990 Allen .................... A61B 90/10 606/54
2016/0302870 A1 10/2016 Wilkinson
(Continued)

FOREIGN PATENT DOCUMENTS

WO 2009/007347 A2 1/2009
WO 2012/149548 A2 11/2012
WO 2017/011892 A1 1/2017

OTHER PUBLICATIONS

Patent Cooperation Treaty, International Search Report for International Application No. PCT/SG2021/050376 dated Sep. 15, 2021, 4 pages.
(Continued)

*Primary Examiner* — Amelie R Davis
(74) *Attorney, Agent, or Firm* — Fitch, Even, Tabin & Flannery LLP

(57) ABSTRACT

A method of determining a position of a fiducial marker set including a plurality of fiducial markers is disclosed. The method includes a step of receiving image slices captured by a 3-dimensional (3D) imaging device. The image slices are processed to identify positions of centre points of the respective fiducial markers. Based on the identified positions of the centre points, a virtual Cartesian geometry associated with the fiducial marker set is identified. The virtual Cartesian geometry is represented by a plurality of virtual Cartesian coordinate axes that meet at a virtual origin. A fiducial marker set and a control system are also disclosed.

8 Claims, 5 Drawing Sheets

(56) References Cited

U.S. PATENT DOCUMENTS

| | | | |
|---|---|---|---|
| 2018/0263707 | A1 | 9/2018 | Sela |
| 2020/0405395 | A1 | 12/2020 | Gullotti |

OTHER PUBLICATIONS

Patent Cooperation Treaty, Written Opinion of the International Searching Authority for International Application No. PCT/SG2021/050376 dated Sep. 15, 2021, 4 pages.

Bao et al. Automated fiducial marker detection and fiducial point localization in CT images for lung biopsy image-guided surgery systems. Journal of X-Ray Science and Technology (2019), pp. 417-429.

* cited by examiner

FIDUCIAL MARKER SET, A METHOD OF DETERMINING A POSITION OF THE SAME AND A CONTROL SYSTEM

CROSS-REFERENCE TO RELATED APPLICATIONS

This application is a U.S. national phase application filed under 35 U.S.C. § 371 of International Application Number PCT/SG2021/050376, filed Jun. 28, 2021, designating the United States.

FIELD OF INVENTION

The present invention relates broadly to a fiducial marker set, a method of determining a position of the same and a control system.

BACKGROUND

Image-guided surgery typically utilizes images obtained prior to or during surgical procedures to guide a surgeon performing the procedures. These procedures are usually complicated and require a system including multiple surgical instruments. Surgical instruments such as robotic arms and flexible needles have been introduced to automate the procedures. Generally, images of the surgical instruments are processed for navigation during surgical procedures.

For example, the images of a surgical instrument can be superimposed on the captured image of the patient for tracking the surgical instrument. In another example, one or more markers can be associated with a surgical instrument or the patient and the position data of these markers are obtained to determine the position of the surgical instrument relative to the position of a patient's anatomy.

Some image-guided surgery utilizes preoperative imaging of a patient. In other words, the surgery is not a real-time intervention procedure as there is no linkage to the imaging device during the procedure. This may cause surgical errors because any movement of the patient between the time the image of the patient was taken and the time the surgery is performed would not be considered during the surgery.

Further, there are problems associated with tracking the surgical instruments or anatomy of patients using certain markers. For example, it is found that markers made using some materials with reflective properties or within a certain range of material density may lead to production of image artifacts, which can lead to difficulties in interpreting the images captured by imaging devices. Therefore, a degree of error may exist in tracking the position of the surgical instruments or patient and this may compromise the outcome of the surgery.

A need therefore exists to provide systems and methods that seek to address at least one of the problems above or to provide a useful alternative.

SUMMARY

According to a first aspect of the present invention, there is provided a method of determining a position of a fiducial marker set including a plurality of fiducial markers, the method comprising:

- receiving image slices captured by a 3-dimensional (3D) imaging device;
- processing the image slices to identify positions of centre points of the respective fiducial markers; and

- based on the identified positions of the centre points, identifying a virtual Cartesian geometry associated with the fiducial marker set, wherein the virtual Cartesian geometry is represented by a plurality of virtual Cartesian coordinate axes that meet at a virtual origin.

Processing the image slices may comprise:

- detecting 2-dimensional (2D) circles on the image slices; and
- calculating centre positions of the 2D circles on the image slices to identify positions of the centre points of the respective fiducial markers.

Processing the image slices may comprise:

- combining the image slices from the 3D imaging device to form a 3D image;
- detecting 3D spheres on the 3D image; and
- calculating centre positions of the 3D spheres on the 3D image to identify positions of the centre points of the respective fiducial markers.

Identifying the virtual Cartesian geometry associated with the fiducial marker set may comprise:

- based on the identified positions of the centre points, measuring distances between the centre points of the plurality of fiducial markers; and
- based on the measured distances, identifying the virtual origin and virtual Cartesian coordinate axes of the virtual Cartesian geometry.

The method may further comprise:

- comparing the measured distances between the identified positions of the centre points with stored actual distances between the centre points of the plurality of fiducial markers; and
- based on the comparison, validating the identified positions of the centre points.

The method may further comprise:

- measuring sizes of the plurality of fiducial markers;
- comparing the measured sizes of the plurality of fiducial markers with stored actual sizes of the plurality of fiducial markers; and
- based on the comparison, validating the identified positions of the centre points.

According to a second aspect of the present invention, there is provided a computer readable medium having stored thereon instructions for execution by a processor, wherein the instructions are executable to perform the method as defined in the first aspect.

According to a third aspect of the present invention, there is provided a fiducial marker set comprising:

- a housing configured to be mounted on a surgical instrument, wherein the housing is made of a radiolucent material; and
- a plurality of fiducial markers configured to be attached to the housing,
- wherein each of the plurality of fiducial markers has a spherical shape with a centre point and is made of a radiopaque material,
- wherein the plurality of fiducial markers are arranged such that the centre points define a virtual Cartesian geometry represented by a plurality of virtual Cartesian coordinate axes that meet at a virtual origin.

The radiopaque material may have a density of more than 2000 kg/m$^3$.

The radiopaque material may comprise one or more selected from Polytetrafluoroethylene (PTFE) and titanium.

The radiolucent material may comprise one or more selected from a group consisting of carbon fiber, Acrylonitrile Butadiene Styrene (ABS) or Polyetherimide (PEI).

According to a fourth aspect of the present invention, there is provided a control system comprising:

a processor communicatively coupled with a robot and a 3D imaging device, the 3D imaging device configured to capture image slices within an imaging space, wherein the imaging space comprises a 3D space with a first fixed origin;

a robot comprising a manipulator including an end effector, wherein the robot is configured to move an elongated tool attached to the end effector within a robot space for aligning the elongated tool with an occluded target, and wherein the robot space comprises a 3-dimensional (3D) space with a second fixed origin; and a fiducial marker set mounted on the manipulator of the robot, the fiducial marker set comprising a plurality of fiducial markers, wherein each of the plurality of fiducial markers has a spherical shape with a centre point and is made of a radiopaque material;

wherein the processor is configured to:

process image slices captured by the 3D imaging device to identify positions of the centre points of the respective fiducial markers;

based on the identified positions of the centre points, identify a virtual Cartesian geometry associated with the fiducial marker set, wherein the virtual Cartesian geometry is represented by a plurality of virtual Cartesian coordinate axes that meet at a virtual origin;

based on the virtual Cartesian geometry associated with the fiducial marker set, calibrate the robot by integrating the robot space with the imaging space;

based on the calibration of the robot, process a 3D image of a body containing the target captured by the 3D imaging device to obtain location data of the target in the integrated space; and based on the location data of the target in the integrated space, automatically control the robot to align a longitudinal axis of the elongated tool with the target.

The processor may be configured to:

process the image slices of the fiducial marker set to detect 2-dimensional (2D) circles on the image slices; and calculate centre positions of the 2D circles on the image slices to identify positions of the centre points of the respective fiducial markers.

The processor may be configured to:

process the image slices of the fiducial marker set to form a 3D image by combining the image slides from the 3D imaging device;

detect 3D spheres on the 3D image; and calculate centre positions of the 3D spheres on the 3D image to identify positions of the centre points of the respective fiducial markers.

The processor may be configured to:

based on the identified positions of centre points, measure distances between the centre points of the plurality of fiducial markers; and based on the measured distances, identify the virtual origin and virtual Cartesian coordinate axes of the virtual Cartesian geometry.

The processor may be configured to:

compare the measured distances between the identified positions of the centre points with stored actual distances between the centre points of the plurality of fiducial markers; and based on the comparison, validate the identified positions of the centre points.

The processor may be configured to:

measure sizes of the plurality of fiducial markers;

compare the measured sizes of the plurality of fiducial markers and stored actual sizes of the plurality of fiducial markers; and based on the comparison, validate the identified positions of centre points.

The processor may be configured to:

based on virtual origin of the virtual Cartesian geometry, calculate a first directional vector between the first fixed origin and the virtual origin;

combine the first directional vector and a second directional vector between the virtual origin and the second fixed origin of the robot to calculate a resultant vector between the first fixed origin of the 3D imaging device and the second fixed origin of the robot; and based on the calculated resultant vector, determine a common origin to integrate the robot space and the imaging space.

The processor may be configured to:

process the 3D image of the body to extract position data of the target in the imaging space; and based on the calibration of the robot, convert the position data of the target in the imaging space into the location data of the target in the integrated space.

BRIEF DESCRIPTION OF THE DRAWINGS

Embodiments of the invention are provided by way of example only, and will be better understood and readily apparent to one of ordinary skill in the art from the following written description and the drawings, in which.

DETAILED DESCRIPTION

Figure 1:
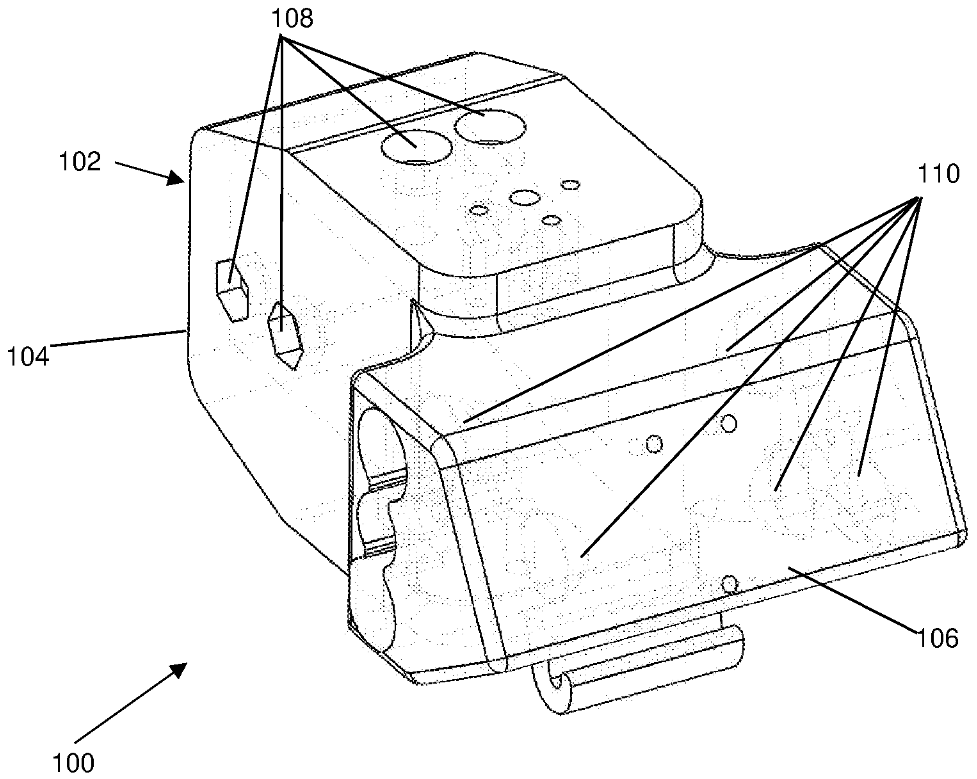
FIG. 1 shows a schematic diagram illustrating a fiducial marker set according to an example embodiment.

FIG. 1 shows a schematic diagram illustrating a fiducial marker set 100 according to an example embodiment. The fiducial marker set 100 includes a housing 102 made of a radiolucent material such as carbon fiber, Acrylonitrile Butadiene Styrene (ABS) or Polyetherimide (PEI). The housing 102 includes a container 104 with a hinged lid 106 covering an opening of the container 104. The container 104 includes several apertures 108 that allows the housing 102 to be mounted on a surgical instrument.

The fiducial marker set 100 further includes a plurality of fiducial markers, represented as five fiducial markers 110 in FIG. 1, attached to the housing 102 in a space defined by the container 104 and the hinged lid 106. The fiducial markers 110 are made of a radiopaque material such as Polytetrafluoroethylene (PTFE) or titanium, and are locatable by a 3-dimensional (3D) imaging device that can produce computer-processed 3D images. It should be noted that the fiducial marker set 100 having five fiducial markers 110 is only an example implementation and the fiducial marker set 100 can have three, four or more fiducial markers 110. The fiducial markers 110 can also be made of a selected radiopaque material with a density of more than 2000 kg/m$^3$.

In one example implementation, each of the fiducial markers 110 has a spherical shape with a 5-20 mm diameter and a centre point. The fiducial markers 110 are arranged in the housing 102 such that the centre points of the fiducial markers 110 define a virtual (or secondary) Cartesian geometry (i.e. a Cartesian coordinate system) represented by a plurality of virtual Cartesian coordinate axes that meet at a virtual origin. The true (or primary) origin may be set, for example, at a base of a robot, as will be described below with reference to FIGS. 3A-3B and understood by a person skilled in the art.

For example, one of the centre points defines the virtual origin of the virtual Cartesian geometry and another three centre points are spaced from the virtual origin at three different predetermined distances defining x, y and z axes of the fiducial marker set 100. With this arrangement, the origin and x, y and z axes can be identified by measuring the distances between the centre points on the images captured by the 3D imaging device, allowing a position of the fiducial marker set 100 to be determined. The remaining one centre point may define an additional axis with the virtual origin to determine the position of the fiducial marker set 100 or to validate the identified virtual Cartesian geometry.

Figure 2:
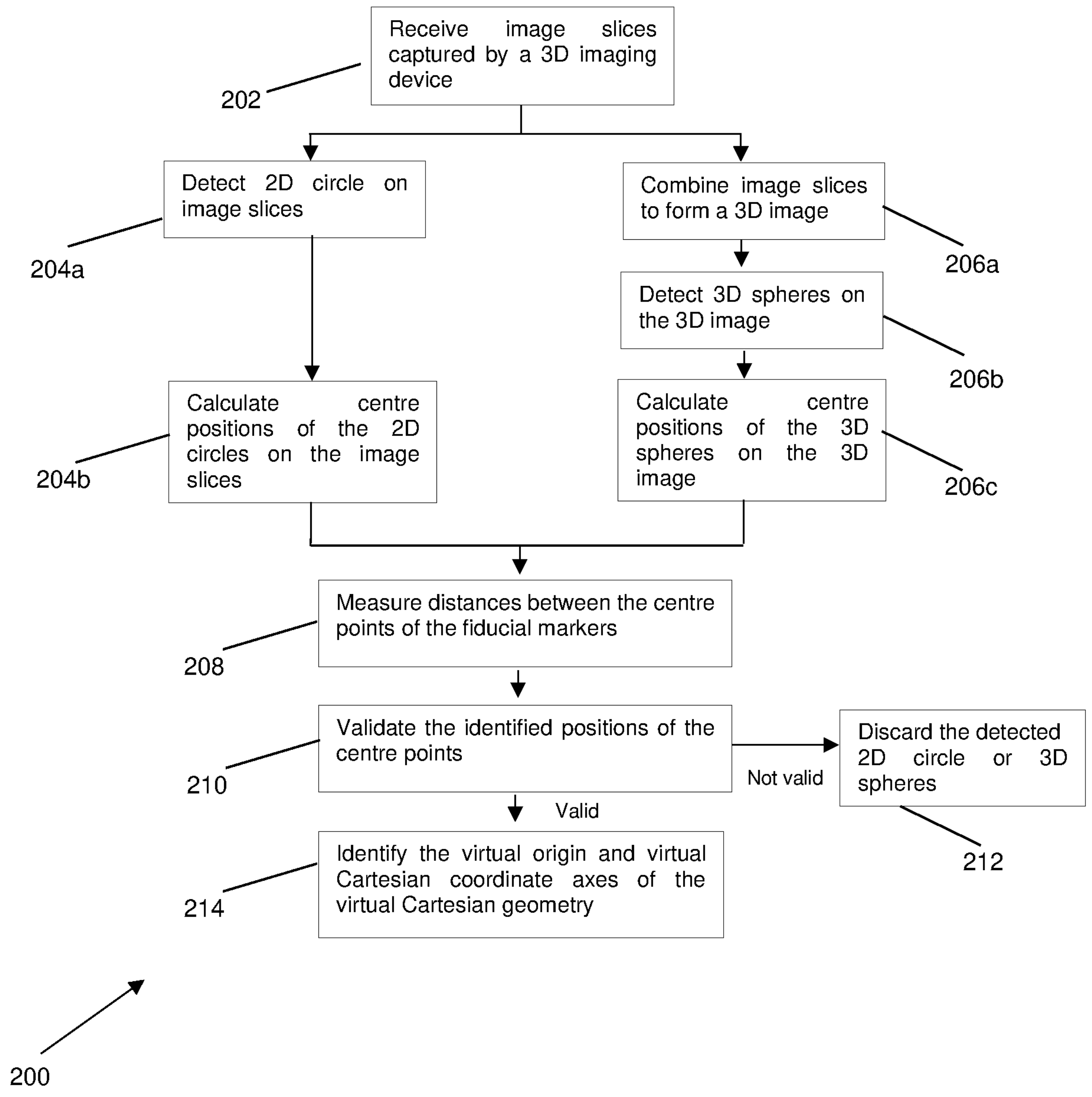
FIG. 2 shows a flowchart illustrating a method of determining a position of a fiducial marker set.

FIG. 2 shows a flowchart 200 illustrating a method of determining a position of a fiducial marker set. In the description that follows, it is explained that the method is performed to determine a position of the fiducial marker set 100 of FIG. 1. It will be appreciated that the method can be performed to determine positions of other types of fiducial markers. Further, the method can be performed by a processor based on instructions stored in a computer readable medium.

At step 202, the processor receives image slices of the fiducial marker set 100 captured by the 3D imaging device. For example, relative to a human body, the image slices can be obtained from the sagittal, coronal or transverse scanning plane at a scanning interval between 0.5 to 3 mm. Next, the image slices are processed to identify positions of the centre points of the fiducial markers 110. This can be completed using 2D image slices (steps 204*a* and 204*b*) or a 3D image formed by the image slices (steps 206*a*, 206*b*, 206*c*).

At step 204*a*, the processor detects 2-dimensional (2D) circles on the image slices using circle Hough Transform (CHT). For example, an algorithm for detecting circles performed by artificial intelligence may be applied. The image of each fiducial marker maybe sliced into multiple sections and the sections are illustrated as 2D circles in multiple image slices. In that case, the processor detects and mathematically interpret the 2D circle with the largest diameter among the image slices by scanning the 2D images in different planes (for example: sagittal, coronal or transverse scanning plane) and multiple slices as well as referring the scanning diameter to the actual diameter of the sphere. This step is repeated until five 2D circles, with the largest diameter and closest to the actual physical diameter of the sphere, which are representative of the five fiducial markers 110 are detected. At step 204*b*, the processor calculates centre positions of the five 2D circles on the image slices to identify positions of the centre points of the five fiducial markers 110.

At step 206*a*, the processor combines the image slices from the 3D imaging device to form a 3D reconstructed image. At step 206*b*, the processor detects five 3D spheres on the 3D image using a 3D image processing technique. For example, an algorithm for detecting round/spherical shapes performed by artificial intelligence may be applied. At step 206*c*, the processor calculates centre positions of the 3D spheres on the 3D image to identify positions of the centre points of all the five fiducial markers 110.

Based on the positions of the centre points, the processor identifies a virtual Cartesian geometry associated with the fiducial marker set 100 to determine the position of the fiducial marker set (steps 208, 210, 212 and 214). At step 208, the processor measures distances between the centre points of the fiducial markers based on the positions of the centre points obtained in steps 204 or 206. At step 210, the processor compares the measured distances between the identified positions of the centre points with the stored actual distances between the centre points of the fiducial markers 110.

Based on the comparison, the processor validates the identified positions of the centre points. If the identified positions of the centre points are not valid, the processor proceeds to step 212 to discard the detected 2D circles or 3D sphere. If the identified positions of the centre points are valid, the processor proceeds to step 214 to identify the virtual origin and virtual Cartesian coordinate axes of the virtual Cartesian geometry as defined by the centre points. The virtual Cartesian geometry represented by the virtual origin and virtual Cartesian coordinate axes can be used to determine the position of the fiducial marker set 100.

In an embodiment, the processor also processes the image slices to measure sizes of the fiducial markers 110. At step 210, in addition to the distances, the processor also compares the measured sizes of the fiducial markers 110 with stored actual sizes of the fiducial markers 110. Based on the comparison, the processor validates the identified positions of the centre points and, proceed with step 212 if the identified positions of the centre points are not valid or proceed with step 214 if the identified positions of the centre points are valid.

Figure 3A:
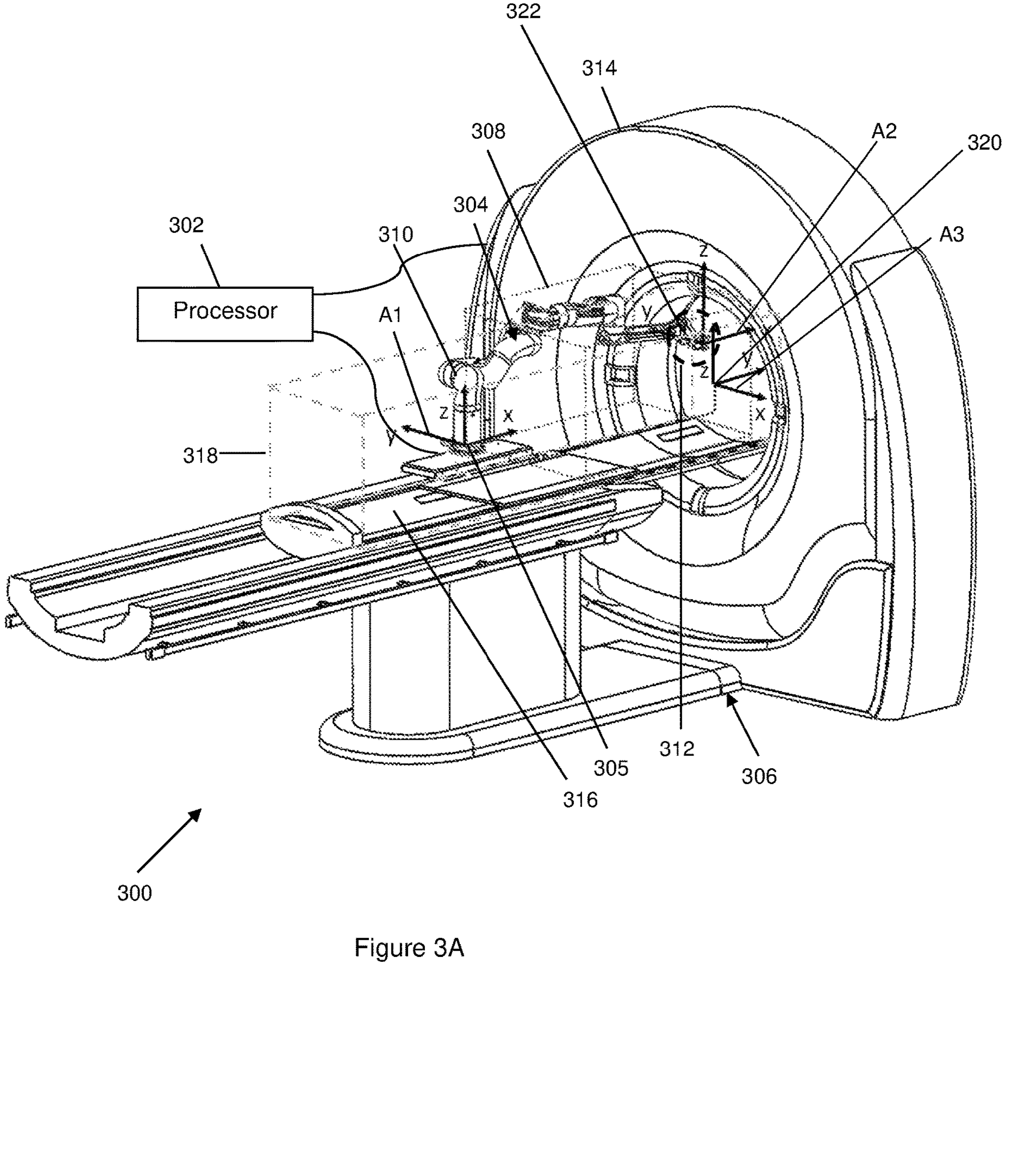
FIG. 3A shows a schematic diagram illustrating a control system according to an example embodiment.
Figure 3B:
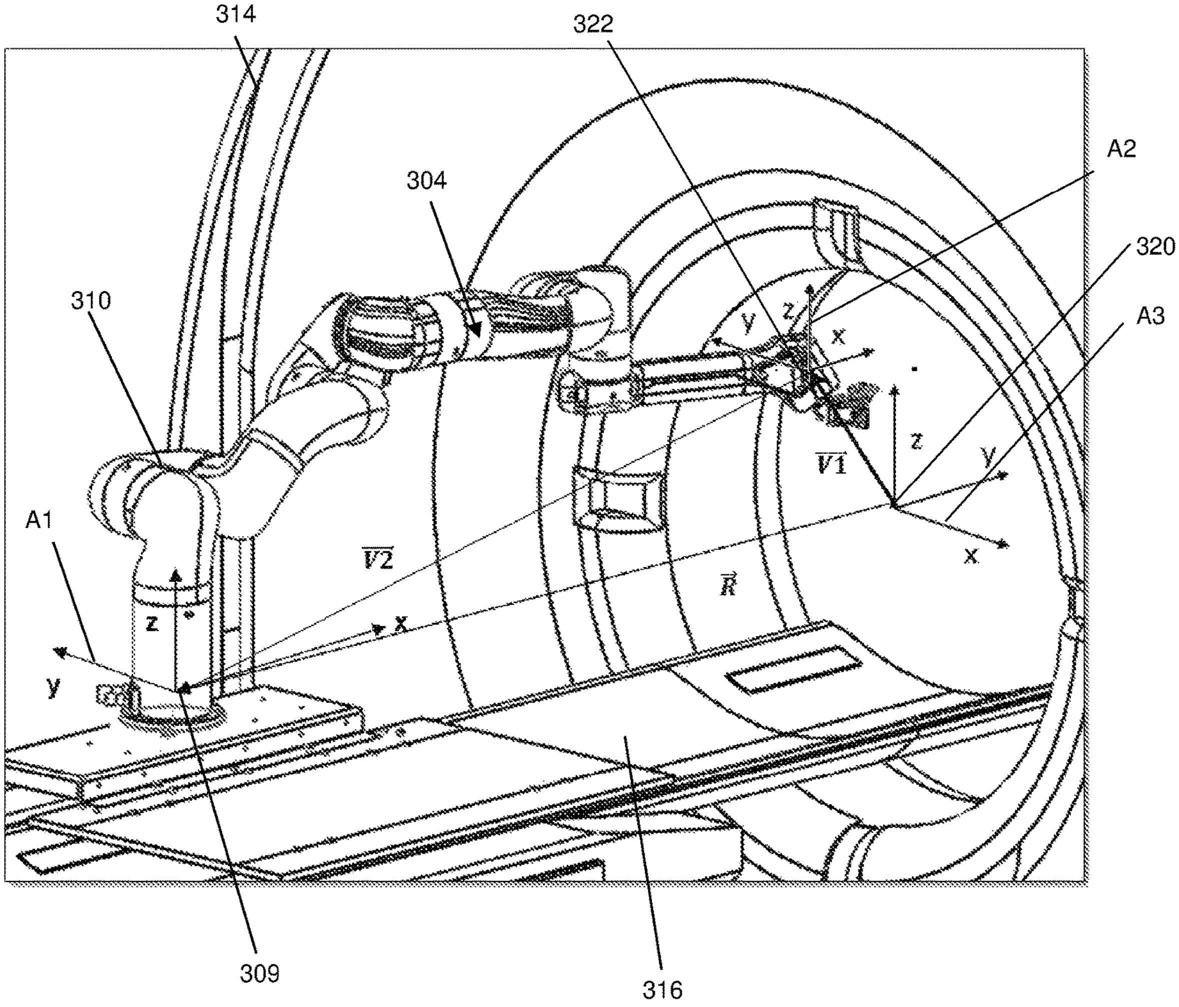
FIG. 3B shows an enlarged view of the system of FIG. 3A.

FIG. 3A shows a schematic diagram illustrating a control system 300 according to an example embodiment. FIG. 3B shows an enlarged view of the system 300 of FIG. 3A. In the description that follows, it is explained that the system 300 is used to align an elongated surgical tool in a surgery performed on a patient's body for treatment of a lesion inside the body. It will be appreciated that the system 300 can also be used in applications other than lesion treatments, such as kidney stone removal and vertebroplasty. Other non-surgical applications are also possible, as will be appreciated by a person skilled in the art.

As shown in FIG. 3A, the system 300 includes a processor 302 communicatively coupled to a robot 304 and a 3-dimensional (3D) imaging device 306. The robot 304 is configured to move within a 3D space (i.e. hereinafter referred to as "robot space 308") having a fixed true (or primary) origin 305 where x, y and z axes meet. The movement of the robot 304 is represented with coordinate axes A1 in FIG. 3A. Based on 3D images captured by the 3D imaging device 306, the robot 304 is controlled by the processor 302 to align the surgical tool to the lesion. The movement of the robot 304 is operated by an actuator (not shown) that receives signals from the processor 302.

In an embodiment, the robot 304 includes a manipulator 310 movable relative to the fixed origin 305. The manipulator 310 has an end effector 312 for holding the surgical tool. The manipulator 310 moves along the coordinate axes A1 as shown in FIGS. 3A and 3B.

The 3D imaging device 306 in example embodiments is a medical imaging device that can perform scanning of the patient's body for producing computer-processed 3D images. Some non-limiting examples of the 3D imaging device 306 include magnetic resonance imaging (MRI) machine, computerized tomography (CT) scanner and fluoroscope. As shown in FIG. 3A, the 3D imaging device 306 includes a gantry 314 which has an x-ray tube and a bed 316 that can be moved into the gantry 314 while the x-ray tube rotates around the patient on the bed 316. The 3D imaging device 306 is configured to capture 3D image within a 3D space (hereinafter referred to as "imaging space 318"). The imaging space 318 is represented with coordinate axes A3 in FIGS. 3A and 3B with a fixed origin 320 where the x, y and z axes meet.

The system 300 further includes a fiducial marker set mounted on the manipulator 310 at a position adjacent to the end effector 312, represented as position 322 in FIGS. 3A and 3B. The fiducial marker set includes a plurality of fiducial markers made of a radiopaque material and are locatable by the 3D imaging device 306. Each of the fiducial markers has spherical shape with 5-20 mm diameter and a centre point. An example implementation of the fiducial market set has been described above with reference to FIG. 1.

In use, the 3D imaging device 306 scans the imaging space 318 to produce image slices. The processor 302 processes the image slices to identify positions of the centre points of the respective fiducial markers. The description about processing the image slices to identify positions of the centre points of the respective fiducial markers has been explained in detail above with respect to steps 204 and 206 of FIG. 2. Next, based on the identified positions of the centre points, the processor 302 identifies a virtual Cartesian geometry A2 associated with the fiducial marker set. The description about identifying a virtual Cartesian geometry A2 associated with the fiducial marker set has been explained in detail above with respect to steps 208, 210, 212 and 214 of FIG. 2.

Based on the virtual origin of the virtual Cartesian geometry A2, the processor 302 calibrates the robot 304 by integrating the robot space 308 with the imaging space 318. Specifically, the processor 302 calculates a first directional vector V1 between the fixed origin 320 of the 3D imaging device 306 and the virtual origin. Further, the processor 302 calculates a second directional vector V2 between the virtual origin and the fixed true origin 305 of the robot 304. The first directional vector V1 and second directional vector V2 are combined to calculate a resultant vector R between the fixed origin 320 of the 3D imaging device 306 and the fixed true origin 305 of the robot 304. Based on the calculated resultant vector R, the processor 302 determines a common origin for integration of the robot space 308 and imaging space 318. In an embodiment, the common origin is at the same point as the fixed origin 320 of the 3D imaging device 306. However, it will be appreciated that the common origin can be located at any other point in a global coordinate system.

Subsequently, the robot 304 is tucked away to the side of the 3D imaging device 306 for the 3D imaging device 304 to scan the patient's body containing the lesion. Based on the calibration of the robot 304, the processor 302 processes the 3D image of the body to obtain location data of the lesion in the integrated space. In an embodiment, the processor 302 processes the 3D image of the body to extract position data of the lesion in the imaging space 318 and based on the calibration of the robot 304, converts the position data in the imaging space 318 into the location data of the lesion in the integrated space.

The processor 302 includes a software to process 3D images from the 3D imaging device 306 to obtain position of body parts, including the body surface, occlusions inside the body (e.g. other organs, bones, arteries) and the lesion. For example, in oncologic imaging, a lesion typically has a richer blood supply than normal body cells which causes an identifiable shade to be generated on 3D images. This allows the software to identify the image of the lesion based on the shades on the 3D images. It will be appreciated that, instead of identifying the lesion using software, the lesion on the 3D image may also be manually identified by a clinician on a display device.

After the location data of the lesion is obtained, the robot 304 is returned to its previous position and above the patient's body. Based on the location data of the lesion, the processor 302 automatically controls the manipulator 310 and end effector 312 to adjust the angular orientation of the surgical tool to align a longitudinal axis of the surgical tool with the lesion. To perform this step, the 3D imaging device 306 captures real-time 3D images of the fiducial markers, and based on the fixed geometrical relationship between the fiducial marker set and the end effector 312 holding the surgical tool, the robot 304 can track and move the end effector 312 to align a longitudinal axis of the surgical tool with the lesion.

After aligning the surgical tool, the processor 302 calculates a striking distance between the tip of the surgical tool and the lesion. In an embodiment, the processor 302 simulates a trajectory of the surgical tool toward the lesion based on the calculated distance. If the simulation result is satisfactory, the clinician confirms to proceed with the insertion of the surgical tool towards the lesion, either by automatic insertion controlled by the processor 302 or manual insertion controlled by the clinician. Upon receiving confirmation to proceed, the processor 302 sends signals to the actuator to advance the surgical tool toward the lesion based on the calculated striking distance. Further images of the fiducial marker set may be captured while advancing the surgical tool toward the lesion in order to make any real-time adjustments, if necessary.

Embodiments of the present invention provide a fiducial marker set 100 and a method of determining a position of the same. Advantageously, the fiducial markers 110 are spherical in shape and do not have a shaft for attachment to the housing 102. This may minimize image artifacts (e.g. beam hardening and scattered radiation) on images produced by the 3D imaging device caused by non-uniform shape of a fiducial marker with a shaft. The fiducial marker set can be tracked with image slices captured by a 3D imaging device and the virtual Cartesian geometry A2 represented by a plurality of virtual Cartesian coordinate axes that meet at a virtual origin can be determined.

Embodiments of the present invention further provide a control system including the fiducial marker set. Using the position of the fiducial marker set, the processor 302 can perform on-the spot calibration of the robot 304 by integrating the robot space 308 and imaging space 318. Due to the calibration, the processor 302 can control the robot 304 to reach a position in the integrated space accurately. This may advantageously enhance the accuracy in the movement of the robot 304, thus reducing the chances of errors in surgical procedures.

Figure 4:
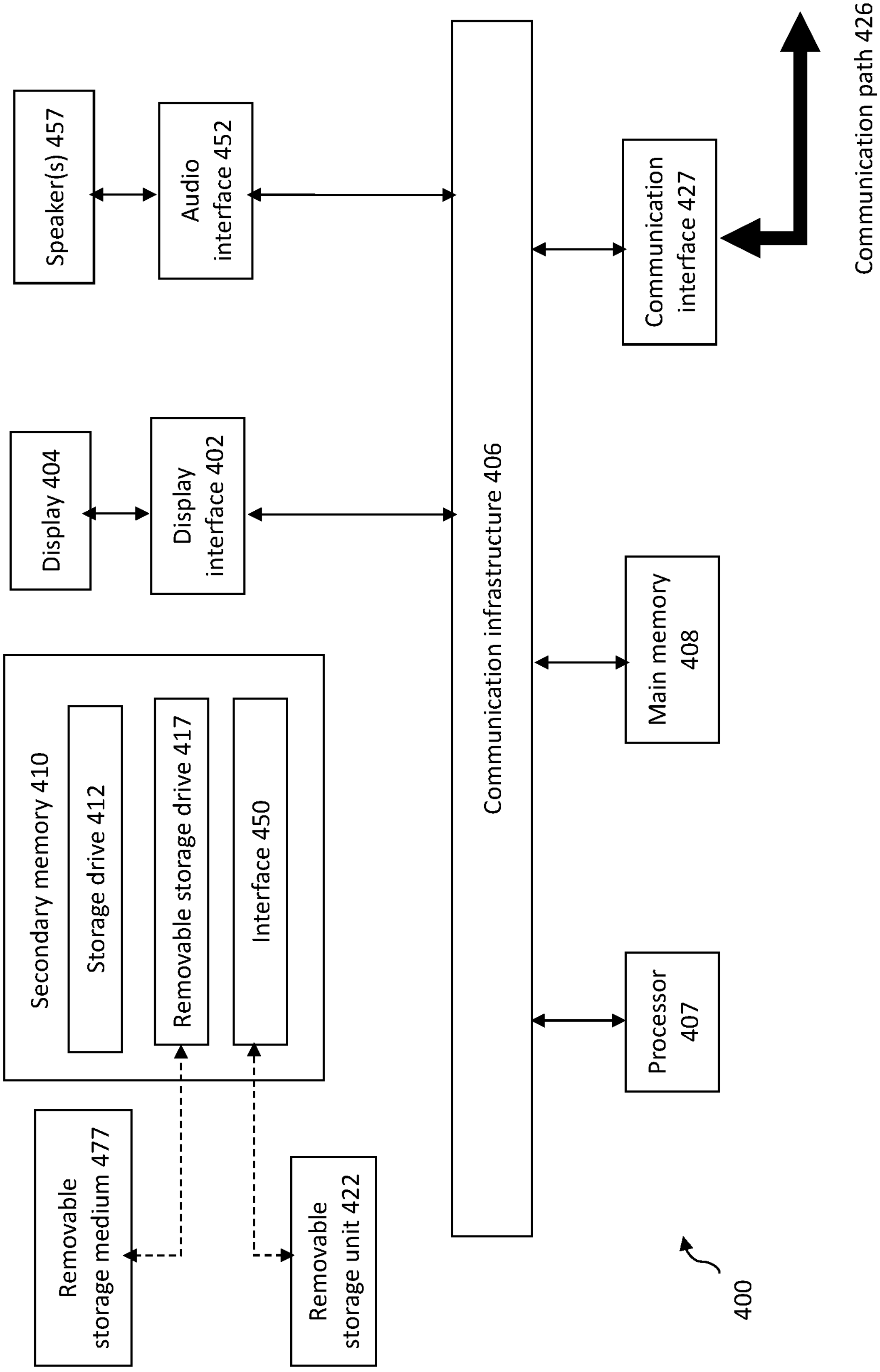
FIG. 4 shows a schematic diagram illustrating a computer suitable for implementing the system and method of the example embodiments.

FIG. 4 depicts an exemplary computing device 400, hereinafter interchangeably referred to as a computer system 400. The exemplary computing device 400 can be used to implement the process shown in FIG. 2 and the system 300 shown in FIGS. 3A and 3B. The following description of the computing device 400 is provided by way of example only and is not intended to be limiting.

As shown in FIG. 4, the example computing device 400 includes a processor 407 for executing software routines. Although a single processor is shown for the sake of clarity, the computing device 400 may also include a multi-processor system. The processor 407 is connected to a communication infrastructure 406 for communication with other components of the computing device 400. The communication infrastructure 406 may include, for example, a communications bus, cross-bar, or network.

The computing device 400 further includes a main memory 408, such as a random access memory (RAM), and a secondary memory 410. The secondary memory 410 may include, for example, a storage drive 412, which may be a hard disk drive, a solid state drive or a hybrid drive, and/or a removable storage drive 417, which may include a magnetic tape drive, an optical disk drive, a solid state storage drive (such as a USB flash drive, a flash memory device, a solid state drive or a memory card), or the like. The removable storage drive 417 reads from and/or writes to a removable storage medium 477 in a well-known manner. The removable storage medium 477 may include magnetic tape, optical disk, non-volatile memory storage medium, or the like, which is read by and written to by removable storage drive 417. As will be appreciated by persons skilled in the relevant art(s), the removable storage medium 477 includes a computer readable storage medium having stored therein computer executable program code instructions and/or data.

In an alternative implementation, the secondary memory 410 may additionally or alternatively include other similar means for allowing computer programs or other instructions to be loaded into the computing device 400. Such means can include, for example, a removable storage unit 422 and an interface 450. Examples of a removable storage unit 422 and interface 450 include a program cartridge and cartridge interface (such as that found in video game console devices), a removable memory chip (such as an EPROM or PROM) and associated socket, a removable solid state storage drive (such as a USB flash drive, a flash memory device, a solid state drive or a memory card), and other removable storage units 422 and interfaces 450 which allow software and data to be transferred from the removable storage unit 422 to the computer system 400.

The computing device 400 also includes at least one communication interface 427. The communication interface 427 allows software and data to be transferred between computing device 400 and external devices via a communication path 426. In various embodiments of the inventions, the communication interface 427 permits data to be transferred between the computing device 400 and a data communication network, such as a public data or private data communication network. The communication interface 427 may be used to exchange data between different computing devices 400 which such computing devices 400 form part an interconnected computer network. Examples of a communication interface 427 can include a modem, a network interface (such as an Ethernet card), a communication port (such as a serial, parallel, printer, GPIB, IEEE 1394, RJ45, USB), an antenna with associated circuitry and the like. The communication interface 427 may be wired or may be wireless. Software and data transferred via the communication interface 427 are in the form of signals which can be electronic, electromagnetic, optical or other signals capable of being received by communication interface 427. These signals are provided to the communication interface via the communication path 426.

As shown in FIG. 4, the computing device 400 further includes a display interface 402 which performs operations for rendering images to an associated display 404 and an audio interface 452 for performing operations for playing audio content via associated speaker(s) 457.

As used herein, the term "computer program product" may refer, in part, to removable storage medium 477, removable storage unit 422, a hard disk installed in storage drive 412, or a carrier wave carrying software over communication path 426 (wireless link or cable) to communication interface 427. Computer readable storage media refers to any non-transitory, non-volatile tangible storage medium that provides recorded instructions and/or data to the computing device 400 for execution and/or processing. Examples of such storage media include magnetic tape, CD-ROM, DVD, Blu-Ray™ Disc, a hard disk drive, a ROM or integrated circuit, a solid state storage drive (such as a USB flash drive, a flash memory device, a solid state drive or a memory card), a hybrid drive, a magneto-optical disk, or a computer readable card such as a PCMCIA card and the like, whether or not such devices are internal or external of the computing device 400. Examples of transitory or non-tangible computer readable transmission media that may also participate in the provision of software, application programs, instructions and/or data to the computing device 400 include radio or infra-red transmission channels as well as a network connection to another computer or networked device, and the Internet or Intranets including e-mail transmissions and information recorded on Websites and the like.

The computer programs (also called computer program code) are stored in main memory 408 and/or secondary memory 410. Computer programs can also be received via the communication interface 427. Such computer programs, when executed, enable the computing device 400 to perform one or more features of embodiments discussed herein. In various embodiments, the computer programs, when executed, enable the processor 407 to perform features of the above-described embodiments. Accordingly, such computer programs represent controllers of the computer system 400.

Software may be stored in a computer program product and loaded into the computing device 400 using the removable storage drive 417, the storage drive 412, or the interface 450. The computer program product may be a non-transitory computer readable medium. Alternatively, the computer program product may be downloaded to the computer system 400 over the communications path 426. The software, when executed by the processor 407, causes the computing device 400 to perform functions of embodiments described herein.

It is to be understood that the embodiment of FIG. 4 is presented merely by way of example. Therefore, in some embodiments one or more features of the computing device 400 may be omitted. Also, in some embodiments, one or more features of the computing device 400 may be combined together. Additionally, in some embodiments, one or more features of the computing device 400 may be split into one or more component parts.

When the computing device 400 is configured to determine a position of a fiducial marker set including a plurality of fiducial markers, the computing system 400 will have a nontransitory computer readable medium having stored thereon an application which when executed causes the computing system 400 to perform steps comprising: receiving image slices captured by a 3-dimensional (3D) imaging device; processing the image slices to identify positions of the centre points of the respective fiducial markers; and based on the identified positions of the centre points, identifying a virtual Cartesian geometry associated with the fiducial marker set, wherein the virtual Cartesian geometry is represented by a plurality of Cartesian coordinate axes that meet at a virtual origin.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

The invention claimed is:

1. A control system comprising:

a processor communicatively coupled with a robot and a 3D imaging device, the 3D imaging device configured to capture image slices within an imaging space, wherein the imaging space comprises a 3D space with a first fixed origin;

a robot comprising a manipulator including an end effector, wherein the robot is configured to move an elongated tool attached to the end effector within a robot space for aligning the elongated tool with an occluded target, and wherein the robot space comprises a 3-dimensional (3D) space with a second fixed origin; and a fiducial marker set mounted on the manipulator of the robot, the fiducial marker set comprising a plurality of fiducial markers, wherein each of the plurality of fiducial markers has a spherical shape with a centre point and is made of a radiopaque material;

wherein the processor is configured to:

process image slices captured by the 3D imaging device to identify positions of the centre points of the respective fiducial markers;

based on the identified positions of the centre points, identify a virtual Cartesian geometry associated with the fiducial marker set, wherein the virtual Cartesian geometry is represented by a plurality of virtual Cartesian coordinate axes that meet at a virtual origin;

based on the virtual Cartesian geometry associated with the fiducial marker set, calibrate the robot by integrating the robot space with the imaging space;

based on the calibration of the robot, process a 3D image of a body containing the target captured by the 3D imaging device to obtain location data of the target in the integrated space; and based on the location data of the target in the integrated space, automatically control the robot to align a longitudinal axis of the elongated tool with the target.

2. The control system as claimed in claim 1, wherein the processor is configured to:

process the image slices of the fiducial marker set to detect 2-dimensional (2D) circles on the image slices; and calculate centre positions of the 2D circles on the image slices to identify positions of the centre points of the respective fiducial markers.

3. The control system as claimed in claim 2, wherein the processor is configured to:

measure sizes of the plurality of fiducial markers;

compare the measured sizes of the plurality of fiducial markers and stored actual sizes of the plurality of fiducial markers; and based on the comparison, validate the identified positions of centre points.

4. The control system as claimed in claim 1, wherein the processor is configured to:

process the image slices of the fiducial marker set to form a 3D image by combining the image slices from the 3D imaging device;

detect 3D spheres on the 3D image; and calculate centre positions of the 3D spheres on the 3D image to identify positions of the centre points of the respective fiducial markers.

5. The control system as claimed in claim 1, wherein the processor is configured to:

based on the identified positions of centre points, measure distances between the centre points of the plurality of fiducial markers; and based on the measured distances, identify the virtual origin and virtual Cartesian coordinate axes of the virtual Cartesian geometry.

6. The control system as claimed in claim 5, wherein the processor is configured to:

compare the measured distances between the identified positions of the centre points with stored actual distances between the centre points of the plurality of fiducial markers; and based on the comparison, validate the identified positions of the centre points.

7. The control system as claimed in claim 1, wherein the processor is configured to:

based on virtual origin of the virtual Cartesian geometry, calculate a first directional vector between the first fixed origin and the virtual origin;

combine the first directional vector and a second directional vector between the virtual origin and the second fixed origin of the robot to calculate a resultant vector between the first fixed origin of the 3D imaging device and the second fixed origin of the robot; and based on the calculated resultant vector, determine a common origin to integrate the robot space and the imaging space.

8. The control system as claimed in claim 1, wherein the processor is configured to:

process the 3D image of the body to extract position data of the target in the imaging space; and based on the calibration of the robot, convert the position data of the target in the imaging space into the location data of the target in the integrated space.

* * * * *